(12) United States Patent
Niazi (10) Patent No.: US 9,469,671 B2
(45) Date of Patent: Oct. 18, 2016

(54) CLOSED BIOREACTOR

(75) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 1351 days.

(21) Appl. No.: 13/312,983

(22) Filed: Dec. 6, 2011

(65) Prior Publication Data

US 2012/0077243 A1    Mar. 29, 2012

(51) Int. Cl.
| | | |
|---|---|---|
| *C12M 3/00* | (2006.01) | |
| *C07K 1/14* | (2006.01) | |
| *B01J 20/28* | (2006.01) | |
| *C07K 1/16* | (2006.01) | |
| *C07K 1/18* | (2006.01) | |
| *C07K 1/20* | (2006.01) | |
| *C07K 1/22* | (2006.01) | |
| *C12M 1/00* | (2006.01) | |
| *C12M 1/12* | (2006.01) | |
| *C12M 1/34* | (2006.01) | |
| *B01D 15/22* | (2006.01) | |
| *C12M 3/06* | (2006.01) | |

(52) U.S. Cl.
CPC .............. *C07K 1/14* (2013.01); *B01J 20/2805* (2013.01); *C07K 1/165* (2013.01); *C07K 1/18* (2013.01); *C07K 1/20* (2013.01); *C07K 1/22* (2013.01); *C12M 23/26* (2013.01); *C12M 29/20* (2013.01); *C12M 29/24* (2013.01); *C12M 37/02* (2013.01); *C12M 41/34* (2013.01); *B01D 15/22* (2013.01); *C12M 27/16* (2013.01)

(58) Field of Classification Search
CPC ............................ C12M 29/00; C12M 33/00

USPC .......................................... 435/289.1; 422/79
See application file for complete search history.

(56) References Cited

U.S. PATENT DOCUMENTS

| 6,544,788 B2 | 4/2003 | Singh | |
|---|---|---|---|
| 2008/0032380 A1* | 2/2008 | Kleis | ...................... C12M 23/04 435/243 |
| 2011/0117538 A1 | 5/2011 | Niazi | |
| 2011/0198286 A1 | 8/2011 | Niazi | |

FOREIGN PATENT DOCUMENTS

| WO | 00/66706 A1 | 11/2000 |
|---|---|---|
| WO | 2010141992 A1 | 12/2010 |
| WO | 2011062621 A1 | 5/2011 |

OTHER PUBLICATIONS

International Search Report and Written Opinion dated Apr. 30, 2013, for corresponding PCT International Application No. PCT/US2012/065055.
Pierce, Bioprocessing J. 3: 51-56 (2004).
Ling et al., "Improvement of Monoclonal Antibody Production in Hybridoma Cells," Biotechnol. Prog., 19: 158-162 (2003).

(Continued)

*Primary Examiner* — Natalia Levkovich
(74) *Attorney, Agent, or Firm* — Therapeutic Proteins International, LLC; Sarfaraz K. Niazi (57) ABSTRACT

Single-use closed bioreactors with recirculating exhaust gas that can be operated in an uncontrolled environment are reported for the manufacturing of biological products using genetically modified biological cultures that produces carbon dioxide or that requires carbon dioxide in their metabolic process.

11 Claims, 2 Drawing Sheets

(56) References Cited

OTHER PUBLICATIONS

Weber et al., "Optimisation of protein expression and establishment of the Wave Bioreactor for Baculovirus/insect cell culture;" Cytotechnology; 38: 77-85 (2002).
Singh, "Disposable bioreactor for cell culture using wave-induced agitation;" Cytotechology; 30: 149-158 (1999).
Fenge et al., "Agitation, aeration and perfusion modules for cell culture bioreactors," Cytotechnology 11: 233-244 (1993).
Chisti "Animal-cell damage in sparged bioreactors," Trends Biotechnol, 18: 420-432 (2000).
Chalmers et al., "Cells and bubbles in sparged bioreactors," Cytotechnology, 15: 311-320 (1994).
Henzler et al., "Oxygenation of cell cultures," Bioprocess Eng. 9: 61-75 (1993).
Krahe, "Biochchemical Engineering," Reprint from Ullmann's Encyclopedia of Indus. Chem.; VCH Publishers: Weinheim, Germany, vol. 6.
Kunas et al.,"Damage mechanisms of suspended animal cells in agitated bioreactors with and without bubble entrainment," Biotechnology and Bioengineering, 36: 476-483 (1990).
Lee et al., in Handbook of Polymeric Biomaterials, CRC Press, Boca Raton, pp. 581-597 (1995).
Marks, "Equipment design consideration for large scale cell culture," Cytotechnology, 42: 21-33 (2003).
Martens et al. "Lethal events during gas sparging animal cell culture," Biotechnology and Bioengineering, 37: 484-490 (1991).
Meier et al. "Cell death from bursting bubbles; role of cell attachment to rising bubbles in sparged reactors," Biotechnology and Bioengineering, 62: 468-478 (1999).
Michaels et al., "Sparging and agitation-induced injury of cultured animal cells: do cell-to-bubble interactions in the bulk liquid injure cells?" Biotechnology and Bioengineering, 51: 399-409 (1996).
Nehring et al., "Experimental study of a ceramic microsparging aerations system in a pilot scale animal cell culture," Biotechnol. Progress, 20: 1710-1717 (2004).
Nelson et al., "Industrial scale mammalian cell culture, Part I: Bioreactor design consdiderations," BioPharm., 1: 42-46 (1988).
Papoutsakis et al., "Fluid-mechanical damage of animal cells in bioreactors," Tibtech, 9: 427-437 (1991).
Zhang et al., "A comparison of oxygen methods for high-density perfusion cultures of an al cells," Biotechnology and Bioengineering, 41: 685-692 (1993).

* cited by examiner

CLOSED BIOREACTOR

FIELD OF THE INVENTION

The present invention relates to a design of bioreactor that can be used in uncontrolled environment of ISO 14644 Class 9 or higher reduces the cost of bioreactor operations substantially; the invention reports a completely closed system wherein the exhaust gas recirculates within the bioreactor and excess carbon dioxide is removed by chemical absorption and the required tension of oxygen or carbon dioxide maintained in the nutrient media by providing fresh gas supply.

BACKGROUND OF THE INVENTION

Active drug entities are frequently derived from biological cultures including human and animal cells, bacteria, yeast, plant cells, hybridomas and any such biological compositions that are capable of replicating and undergoing metabolism. Additionally, biological entities are grown into organs and products of cell and gene therapy. The biological entities are routinely grown using traditional bioreactors and more recently disposable bioreactors.

Bioreactors are devices that convert nutritional elements into useful products using biological catalysts (biological culture) such as human and animal tissue cells, microorganism, baculoviruses and insect cells, etc. The main function of a bioreactor is to provide a controlled environment for the growth of the biological catalysts to obtain a desired product. A large number of designs of bioreactors are available as evidence by hundreds of patents issued to specific design elements of bioreactors. A variety of vessels and methods have been developed over the years to carry out chemical, biochemical and/or biological processing.

Although bioreactor systems and related processes are well known, improvements to such systems and processes would be useful in the preparation of a variety of products produced from a biological source. One such improvement is the environment where a bioreactor is operated. In the manufacturing of drugs and vaccines, an ISO 14644 Class 8 or Class Area classification of not more than 100,000 particles of 0.5 um per square foot is required. To maintain this air quality, the air is continuously passed through a HEPA filter and about 20 air exchanges per hour are required. To maintain this air quality standard, the HVAC systems, the HEPA filters and continuous air cleaning required adds to substantial capital and energy cost, often making it impossible for small companies or research organizations to produce drugs and vaccine for use in humans. Taking an example of a manufacturing facility requiring an airflow of 1 million cubic meters per hour, operating 24 hours a day for the whole year, and at a utility rate of $0.135 kW/h (Bureau of Labor Statistics, US Government for August 2011), the cost of operating the fans alone will be over half a million dollars. Other significant cost is the HEPA filters that must be replaced periodically, adding another half a million dollars to the total cost. The capital cost of an HVAC system is also very high; approximately $200 per square foot is added for the HVAC systems. In a 100,000 square foot facility, this adds about $20 Million to the cost of a project. While these costs are of lesser significance to large pharmaceutical and biotechnology companies, these form the key barrier to the development of drugs by smaller companies and research institutions, not able to afford these costs.

There are also instances, where a drug or vaccine may need to be manufactured in an emergency and in those instances the requirement of clean room environment impedes development and manufacturing.

There is a dire unmet need to create a bioreactor system that could be operated in a reasonably clean environment without the need for expensive HVAC systems. The atmosphere has about 2.5 million particles per square foot and the room air has about 1 million particles of size 0.5 um or larger. The room air is classified as ISO 14644 Class 9 or Level 1 according to the cGMP guidelines provided by the World Health Organization; it is also labeled as uncontrolled area classification. Reasons for requiring a controlled environment include protecting the product from environment and also protecting the personnel from the product; HVAC systems also prevent cross-contamination and are generally regarded as one of the most significant steps in assuring safety of the manufactured drugs.

To allow a bioreactor to operate in ISO 14644 Class 9 environment, it must have key features that will completely seal the bioreactor from environment for every step of the operation of a bioreactor. Once this can be validated and thus assured that there cannot be any contact between the environment and the contents of a bioreactor, it will be possible to operate these bioreactors in ISO 14644 Class 9 environment. However, bioreactors require supply of nutrition that includes oxygen and carbon dioxide and maintaining a flow inside a bioreactor without contaminating with the environment is a challenge that has not been met satisfactorily.

Prior art points to the system offered by Xcellerex (http://www.xcellerex.com/flexfactory-design.htm) that proposes to use proprietary FlexFactory process train that is comprised of disposables-based unit operations which minimizes the risk of cross-contamination. Each unit operation is enclosed in a controlled environment module (CEM), which is co-located in common, controlled manufacturing space. The CEM provides a localized clean environment around the equipment and with positive pressure to the room. The environmental standards for the FlexFactory CEM's are based on traditional clean room standards. Operators stand outside the CEM and access the equipment access through iris ports. The need for multiple airlocks and gowning and re-gowning rooms is eliminated. While this system provides isolation of operation, the plan is flawed because there is no definite way to assure that a breach in the system will not take place and if it does, then it will immediately contaminate the product. This concept has some applications but it is unlikely that the regulatory agencies would allow use of the FlexFactory for commercial production of biological drugs.

The present invention provided a completely closed bioreactor wherein all inlets are provided through a 0.22-micron filter, the exhaust recirculates and the nutrient medium outlet is kept sealed until the bioreactor is ready for draining. Additionally, all those contacts where a clean room exposure is required such as introduction of biological culture and handling the manufactured product are conducted in controlled environment.

The present invention of a closed bioreactor can be operated without the limitations of the FlexFactory of a physical space where it must be located, it can be of any size, a limitation of FlexFactory, and provides continuous protection of the product from the environment and the environment from the product. The major difference between the FlexFactory and the present invention is that the present invention protects the product directly, while FlexFactory provide a protection around the container holding a product.

The present invention also reports a single-use or disposable bioreactor. The traditional drawbacks in the design of bioreactors have led to the development of disposable bioreactors. During the past ten years, there has been a significant move towards using disposable or single-use bioreactors (SUB) to avoid cross-contamination and reduce the cost of validation (cleaning) between batches; the risk of viral contamination has further hastened the development of these single-use bioreactors. The design of single-use bioreactor can mimic the stirred tank as disposable liners with embedded or magnetically driven stirrers are used while the rocking motion type bioreactors are used without internal stirring. Despite significant development in this field, the utilization of these types of bioreactors has not been very successful for cells or organisms requiring high rates of oxygenation since that would require strong stirring that is not readily possible with disposable systems. Examples of SUBs are systems based on wave agitation. See, e.g., U.S. Pat. No. 6,544,788; PCT Publication WO 00/66706. This type of bioreactor may be used to culture relatively sensitive cells such as CHO cells (e.g., Pierce, *Bioprocessing J.* 3: 51-56 (2004)), hybridoma cells (e.g., Ling et al., *Biotech. Prog.*, 19: 158-162 (2003)), insect cells (e.g., Weber et al., *Cytotech.* 38: 77-85 (2002)) and anchorage-dependent cells (e.g., Singh, *Cytotech.* 30: 149-158 (1999)) in a single disposable container. Such disposable units are relatively cheap, decrease the risk of infection because of their single use and require no internal stirring parts to facilitate gas exchange. More common techniques for mixing the nutrient media include rocking, shaking, vibrating, compressing the walls of the container and in bubble reactors, using gas to stir the liquid.

BRIEF SUMMARY OF THE INVENTION

The bioreactor container of the present invention is designed to grow all types of cells and organisms in an uncontrolled environment (ISO 14644 Class 9). A closed system is provided wherein an adequate amount of nutrients are made available with required gases such as oxygen and carbon dioxide. There are two types of reactions mostly encountered in drug manufacturing, the one where the cells or organisms produce carbon dioxide in the process of their growth such as in the case of bacteria or where cells require carbon dioxide as a source of carbon, such as in the case of mammalian cells.

Where an organism requires oxygen, the end product is often carbon dioxide and that has presented significant challenges to the design of disposable bioreactors for bacterial fermentation since it requires passing a very large volume of air or oxygen through the nutrient media, partly to provide oxygen and partly to remove carbon dioxide (which dissolves in nutrient medium) that is detrimental to the growth of bacteria. High levels of carbon dioxide product produce low pH that is further detrimental to the growth of bacteria. The room air generally contains about 0.035% of carbon dioxide whereas the exhaled human air has about 5% carbon dioxide. Exposure of healthy individuals for prolonged periods of 1.5 percent carbon dioxide will cause mild problems while exposure to 7 percent to 10 percent carbon dioxide will produce unconsciousness within a few minutes. This is because at higher concentrations, carbon dioxide can displace the oxygen in the air. Because of this, carbon dioxide is called a "simple asphyxiant," requiring regulatory standards for require ventilation of manufacturing facilities. For example ASHRAE 62 requires fresh air inlet of at least 0.12 CFM per square foot of floor space.

The air we breathe is made up of mainly four gases: nitrogen (78%), oxygen (21%), argon (0.94%), carbon dioxide (0.04%). When we breathe in air, our bodies consume its oxygen and convert it to carbon dioxide. Exhaled air contains about 4.5-percent carbon dioxide. Our bodies do not do anything with nitrogen or argon. The same is true for biological organisms utilizing oxygen for metabolism. Since there are only two gases that are of importance, oxygen and carbon dioxide, there is no reason why nitrogen and argon cannot be re-used coming out of the exhaust of a bioreactor. This is an inventive step wherein only the useful components in the air are utilized while allowing use of a completely closed system.

Whereas standard bioreactor operations exhaust the effluent gases to environment, the open end of the exhaust creates a permanent risk for contamination of the contents of the bioreactor; it is important to realize that when using disposable flexible containers as bioreactors, it is a likely possibility that the air from the room may be sucked into the container; exhausting gases from bioreactor provide contamination possibilities that may require use of controlled environment. One solution to resolving this problem is to eliminate all exhausts in a bioreactor; instead the air in the bioreactor is recirculated but where carbon dioxide is produced in the nutrient medium, there arises a need to remove carbon dioxide from the air recirculating. There is a large prior art on method for the removal of carbon dioxide from the air or the scrubbing of carbon dioxide from the air. These usually involve using a variant of the Kraft process. Scrubbing processes may be based on sodium hydroxide. First, carbon dioxide is absorbed by an alkaline NaOH solution to produce dissolved sodium carbonate. The carbonate ion is removed from the solution by reaction with calcium hydroxide ($Ca(OH)_2$), which results in the precipitation of calcite ($CaCO3$). The regenerative carbon dioxide removal system (RCRS) on the space shuttle orbiter uses a two-bed system that provides continuous removal of carbon dioxide without expendable products. Regenerable systems allow a shuttle mission a longer stay in space without having to replenish its sorbent canisters. Older lithium hydroxide (LiOH)-based systems, which are non-regenerable, are being replaced by regenerable metal-oxide-based systems. A system based on metal oxide primarily consists of a metal oxide sorbent canister and a regenerator assembly. It works by removing carbon dioxide using a sorbent material and then regenerating the sorbent material. The metal-oxide sorbent is regenerated by pumping air heated to around 400° F. at 7.5 scfm through its canister for 10 hours. Since the present invention is based on a completely closed system, regenerable systems can not be used and provisions are made in the design of the scrubber devices to hold the by products, which is generally water that can be returned to the bioreactor.

Activated carbon can be used as a carbon dioxide scrubber. Various strong bases such as soda lime, sodium hydroxide, potassium hydroxide, and lithium hydroxide are able to remove carbon dioxide by chemically reacting with it. In particular, lithium hydroxide is used aboard spacecraft to remove carbon dioxide from the atmosphere. It reacts with carbon dioxide to make lithium carbonate.

The present invention includes a method for removing carbon dioxide from the effluent gases produced in the bioreactor by installing a cartridge containing a chemical such as soda lime; once the carbon dioxide has been removed, the gases can be brought back into bioreactor (for the purpose of agitating the solution and for oxygenation where required). It is noteworthy that the only components of air that are pertinent to bioreactions are oxygen and carbon dioxide, and thus the ability to manipulate their levels allows recirculation of air in a closed system as these are supplemented by the introduction of fresh gas.

In those bioreactions where a certain quantity of carbon dioxide is required (e.g., mammalian cells), there is no need for a means of removing carbon dioxide from the effluent gases.

Oxygen tension in the nutrient medium is important for many bioreactions and this is controlled in the present invention by providing means of adding oxygen gas (or a mixture of oxygen with air or nitrogen) through a sterilizing filter on a need basis. Sensors in the nutrient medium, which are remotely controlled, allow oxygenation of the nutrient medium as needed. Where a higher level of carbon dioxide is required such as in the case of mammalian cells, the input gas can be a mixture of air and carbon dioxide or pure carbon dioxide; again the purpose of the inlet gases is only to provide a required level of these gases in the nutrient medium while the recirculation of gases within the bioreactor provides the mixing function and also as a means of promoting exit of gases, more particularly carbon dioxide though chemical scrubbing during the recirculation cycle.

The present invention consists of a container that can be constructed from flexible or semi-flexible, waterproof material, preferably plastic. Plastic may be chosen for light transmitting qualities. Certain cells may be sensitive to bright white light or ultraviolet radiation, and for these cells the container can be made of plastics the absorb these wavelengths. Likewise, other kinds of cells, plant cells for example, may be developmentally regulated by the spectral quality of light, and for these cells the culture container can be made of plastics that selectively transmit the desired wavelengths of light. Other characteristics of the material used for making the container may be important in culturing various types of cells or microorganisms. The inside of the container may be treated with substances that increase or decrease cell adhesion, depending on the culture conditions desired and the kind of cells.

In a preferred embodiment, the said container would be made of an inner layer of low density polyethylene, a gas barrier of ethylene vinyl alcohol, outer layer of low density polyethylene and ports made of polyethylene; it will have film thickness of 325 μm, haze 5% (ASTM D-1033), water vapor transmission Rate of 0.4 $g/m^2 \cdot day$ (ASTM F-1249), oxygen permeability of 0.1 $cm^3/m^2 \cdot day \cdot bar$ (ASTM D-3985 (23° C., 0% RH)), carbon dioxide permeability of 0.2 $cm^3/m^2 \cdot day \cdot bar$ (Mocon Permatran C-IV (23° C., 0% RH)) and sterilized by a maximum gamma radiation dose of 50 KGy. The bag will be used at 4° C. to 40° C.

The container comprises one or more ports to serve as inlets or outlets for gases or liquids. The ports are constructed of rigid or semi-rigid materials that are compatible with the material used for construction of the container. In preferred embodiments, any standard plastic tubing or molded plastic can be used to construct the ports, and they are welded into the seams of the container according to standard techniques. A variety of such ports are commercially available, e.g., for use in medical bags and similar containers. The structures that form the ports can also be varied, e.g., to accommodate different volumes of media, autoclave techniques and port functions.

The disposable bioreactors of the present invention preferably are pre-sterilized prior to use. Various sterilization techniques may be used. The choice of technique is partially dependent on the type of plastic chosen (Lee et al., 1995, in Handbook of Polymeric Biomaterials, CRC Press, Boca Raton, p 581-597). Sterilization techniques that are common in the art include, but are not limited to, dry heat, autoclaving, radiation, and ethylene oxide gas.

The bioreactor of the instant invention may be physically supported by several means. The container may be hung by holes in the top of the container outside the seam, or by hooks attached to the top of the container. Alternately, the flexible plastic container may be placed in a rigid outer container including such simple systems as commercial 55-gallon plastic drums. Finally, the container can be constructed of a semi-flexible plastic that can support itself.

The bioreactor can be equipped with optional devices to aid in the growth of culture cells and microorganisms. These devices include, but are not limited to, thermometers, gas evaluation systems (i.e., carbon dioxide or oxygen), and means to evaluate cell density and volume calibration markings.

Air or other gas is introduced into the container via a gas inlet port. Tubing connecting the port to a gas pump is fitted with at least one filter, for filtering microbes from the airstream prior to introduction of the gas into the bioreactor. The tube preferably is adapted for use with a commercially available air pump, with provision to pump a constant amount of air inside the bioreactor regardless of the back-pressure that builds once the culture begins to grow and the density of media increases.

The sparger comprises a tube or a disc of an appropriate diameter depending on the amount of air to be diffused into the container; the sparger is generally constructed of a ceramic or aluminum oxide material, plastic, silicon, or metal. The sparging function is supposed to remove the need to shake or rock the container for mixing purpose. However, in some instances, an external means of shaking the nutrient medium may be necessary. This can be provided by a variety of existing methods such as rocking, shaking, rotating, of pushing on the walls of the container.

The invention further includes an inlet port for filling the bioreactor with growth medium initially or in a perfusion system, recycled media or inoculums.

The liquid port at the top of the containers is typically connected to a dip tube of sufficient length to reach below the working level of media to prevent entry of exhaust gases into this port. This port can also be used for adding nutrients during the process of fermentation (e.g., when using a fed-culture technique) or to provide for replacement of any media removed in the process of perfusion bioreactor operations.

It is noteworthy that the port used to add biological culture, remove nutrient medium at the end of cycle and addition of nutritional feeds is done through a tube that opens in a clean environment at the other end; this can easily be a laminar flow hood installed nearby the bioreactor.

The bioreactor provided in this invention can be used to grow a wide variety of cells including, but not limited to, plant cells, bacteria, yeast, mammalian cells and insect cells. Additional applications can be found in growing organs and creating therapeutic interventions based on individualized medicines. It will be appreciated by one skilled in the art that the composition of the medium and inoculate can be selected to aerobically culture a wide variety of cells and organisms. The temperature of growth, flow of air and duration of culture can also be adjusted to suit specific cells. Other adjustments may include aeration with different gases, e.g., carbon dioxide in the case of plant cells or hydrogen sulfide for sulfur bacteria; or treatment of the bioreactor walls to promote cell adhesion in the case of mammalian cells.

The present invention is not limited to the embodiments described and exemplified above, but is capable of variation and modification without departure from the scope of the appended claims.

DETAILED DESCRIPTION OF INVENTION

The bioreactors are operated generally in ISO 14664 Class 8 environment that is expensive to construct and operate. A closed bioreactor wherein all operations are conducted within the vessel supporting nutrient medium can be used in less controlled or ISO 14644 Class 9 environment that is much cheaper to build and maintain. The present invention provides an ideal solution to expanding the use of bioreactors and making them more affordable. This is of particular value when manufacture drugs and vaccines in emergencies, developing new drugs, manufacturing clinical test supplies and generally producing commercial scale biological drugs at a lower cost. The last consideration has recently become very important, as generic biological drugs have begun appearing in the market following expiry of innovator patents on these drugs. The generic producer must be able to manufacture these molecules at a cheaper cost to compete and this invention fills that need.

In one aspect, the present invention provides a bioreactor suitable for preparing a biological product while operating in an ISO 14664 Class 9 environment from a predetermined volume of nutrient medium, and a related method of use. More particularly, the invention provides an apparatus and method, which is universal in the sense that the apparatus may be used to prepare a biological product regardless of the nature of the biological culture.

Figure 1:
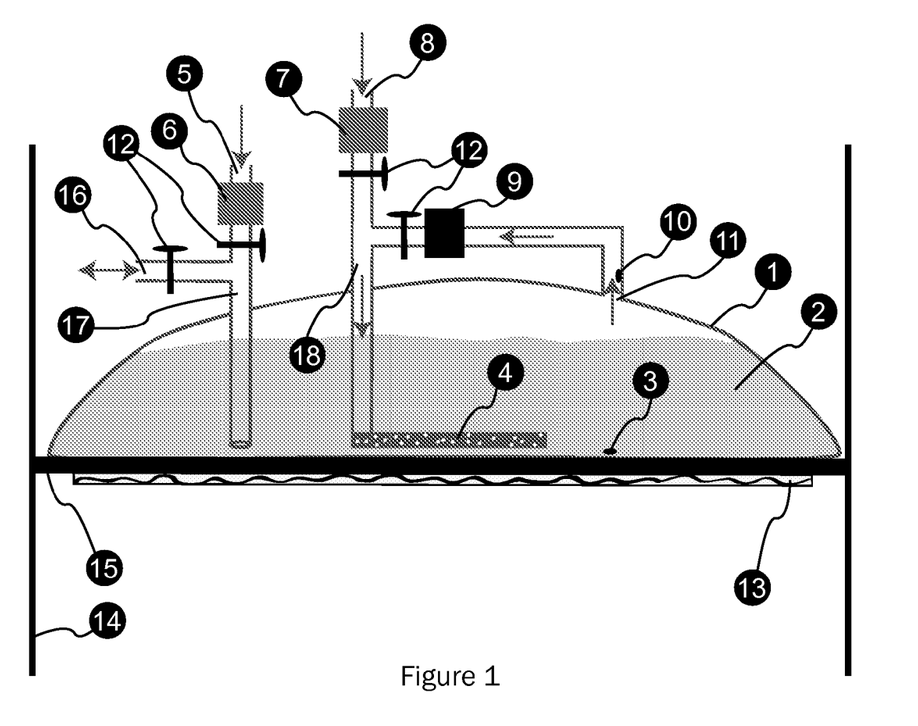
FIG. 1 is a side view of a single-use closed bioreactor for use in reactions that do not require removal of carbon dioxide.

Turning initially to FIG. 1, a preferred embodiment of the inventive bioreactor is illustrated. In this embodiment, there is illustrated a preferred container 1, the interior of this container comprising nutrient medium 2, a fresh air inlet 18 to which is connected at least one means of sparging 4, a source of fresh gas through fresh air inlet 8, a gas sterilizing filter 7 disposed between gas inlet 18 and fresh air inlet 8, and a stopcock 12 between the gas inlet 18 and the sterilizing filter 7, a liquid port 17 connected to a source of nutrient medium through inlet 5, a liquid media sterilizing filter 6 disposed between the inlet 5 and liquid port 17 and a stopcock 12 disposed between the sterilizing filter 6 and the liquid port 17. The exhaust air escapes through gas outlet 11 and moved by using a peristaltic pump 9 and through a stopcock 12 for recirculation through gas inlet 18 and sparger 4. A set of sensors 3 and 10 to monitor carbon dioxide or oxygen are disposed in the container 1 and in the gas outlet 11; the container has a support surface 15, which is in turn supported on a stand 14. A means of heating 13 is provided attached to the lower surface of the support surface 15.

Figure 2:
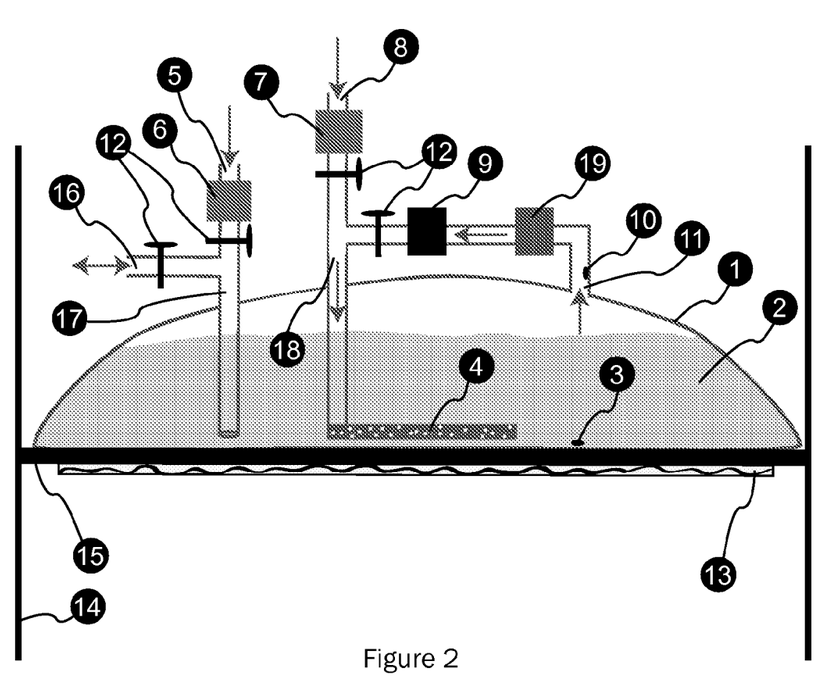
FIG. 2 is a side view of a single-use closed bioreactor for use in reactions that require removal of carbon dioxide.

FIG. 2 shows details of all features in FIG. 1, with additional feature that comprises a carbon dioxide scrubber 19 installed between the gas outlet 11 and the gas inlet 18.

As previously mentioned, the containers desirably include one or more sensors or probes for monitoring one or more process parameters inside the containers such as, for example, cell density, temperature, pressure, pH, dissolved oxygen (DO), dissolved carbon dioxide ($DCO_2$), mixing rate, and gas flow rate. The sensors for DO, pH and $DCO_2$ are desirably optical sensors, with the first two more desirably being disposable (e.g., TruFluor sensors, Finesse Solutions LLC, Santa Clara, Calif. or CellPhase sensors, Fluorometrix Corporation, Stow, Mass. 01775). Each sensor is intended to be in communication with a computer-implemented control system (e.g., a computer) for calculation and control of various parameters and for display and user interface. Such a control system may also include a combination of electronic, mechanical, and/or pneumatic systems to control the aforementioned processing parameters as required to stabilize or control the parameters (e.g., pH may be adjusted by the addition of $CO_2$ or ammonia). It should be appreciated that the control system may perform other functions and the invention is not limited to having any particular function or set of functions.

The one or more control systems described herein can be implemented in numerous ways, such as with dedicated hardware and/or firmware, using a processor that is programmed using microcode or software to perform the functions recited above or any suitable combination of the foregoing.

The processing device may also be in communication with various devices which can adjust the process parameters toward predetermined acceptable levels, for example, activating a heater, activating a gas inlet valve to adjust the oxygen or $CO_2$ levels, activating the gas outlet valve to reduce gas pressure in the headspace, and the like.

Alternately, the invention may be devoid of any sensors and the measurements of the characteristics of culture media made on the sample collected through the port 16, which is also used to introduce biological culture in the container 1 and to remove the nutrient media at the end of the bioreaction cycle. It is noteworthy that port 16 requires an extension long enough to allow delivery of nutrient media for testing or further processing to a controlled environment, likely ISO 14644 Class 7 or lower.

The bioreactor described herein is useful in the production of a biological product from a nutrient medium of a predetermined volume. In a related embodiment, the invention provides a method which contemplates providing a bioreactor as herein described, filling each container with nutrient medium; activating the selectively sparging filter and heating or cooling elements, adding biological culture and allowing the bioreactor to stand for a specific time, detecting the density of cells in the nutrient medium in a container at predetermined time intervals; and removing the nutrient medium and the biological product produced thereby from the bioreactor when the density of the cells in the nutrient medium in the container reaches a predetermined value. The exhaust gases are recirculated through the container while replenished with appropriate quantities of oxygen or carbon dioxide; when carbon dioxide is produced in a bioreaction, a carbon dioxide scrubber is provided to remove carbon dioxide from the exhaust gases.

One of the advantages of the inventive bioreactor and related method is the reduced cost of environmental control required to operate bioreactors. The present invention can be operated in an ISO 14644 Class 9 environment as opposed to Class 8 environment generally required for these operations.

The relatively lower amount of gas introduced (relative to known processes) has the further advantage of generating less turbulence and foam in the headspace of the container.

Each container is provided with a submicron filter that assists in maintaining sterility of the nutrient medium and gases introduced. The filter may be of any suitable size and porosity, but is preferably a HEPA filter, having an average porosity of from about 0.3 µm to about 0.1 µm, and more preferably of about 0.22 µm.

Generally, the invention provides bioreactors and methods, which are universal in the sense that the invention is suitable and adaptable for processing a variety of compositions, including both biologic and non-biologic components. Indeed, an inventive bioreactor designed for use with mammalian cells, for example, may be used for culturing bacteria, allowing ease of manufacturing.

Historically, biological products expressed in nutrient medium are separated from the medium by first removing the biological culture by a process of centrifugation or filtration. This step is followed by reducing the volume of medium to about $\frac{1}{10}$ to $\frac{1}{20}$ to make it possible to load the nutrient medium within a reasonable time on purification columns. While these process steps have been widely validated and function very well, the practicality of using these steps becomes very difficult when large volumes of medium is handled. Today, it is not uncommon to see bioreactors processing thousands and even hundreds of thousands of liters of medium at a time. To accommodate this, companies use very large-scale filtration and volume reduction methods that cost millions of dollars to install and millions more to operate and maintain. There is a very large unmet need to simplify these processes, reduce the cost of production and make the technology accessible to thousands of researchers and smaller companies who cannot afford such large investments. Circumventing these process hurdles will also make it possible to produce drugs based on these biological drugs cheaper to manufacture and thus increase their affordability to billions of people around the world who are not able to afford these drugs.

The key to the present invention lies in following a contrarian teaching. While all manufacturers follow the path described above involving removal of components from a broth ready for purification, it will be prudent to examine the utility of first removing the target biological product instead and discarding what is not needed, instead of removing step by step what is not needed, as currently practiced.

The present invention capitalizes on the recent availability of many resins that are capable of binding biological products in large quantities. Most modern resins will bind between 20-125 mg of biological product per mL of resin. Many of these resins are highly specific to the biological products and many of them can be combined to remove any type and quantity of a biological product from a solution by a simple process of physicochemical binding that is strong enough to retain the biological products attached to the resin while the nutrient medium is removed from the bioreactor. The art has also advanced significantly in the field of biological product purification wherein we now have a much better ability to elute these bound biological products from resins by adjusting the pH, the ionic strength or other characteristics of the eluting buffer to break the binding between the resin and the biological product. This allows removal of biological products from a bioreactor as a highly concentrated solution that is ready for further purification and in some instances it can even be the final product for use.

Affinity chromatography is a separation technique based upon molecular conformation, which frequently utilizes application specific resins. These resins have ligands attached to their surfaces, which are specific for the compounds to be separated. Most frequently, these ligands function in a fashion similar to that of antibody-antigen interactions. This "lock and key" fit between the ligand and its target compound makes it highly specific.

Many membrane proteins are glycobiological products and can be purified by lectin affinity chromatography. Detergent-solubilized proteins can be allowed to bind to a chromatography resin that has been modified to have a covalently attached lectin.

Immunoaffinity chromatography resin employs the specific binding of an antibody to the target biological product to selectively purify the biological product. The procedure involves immobilizing an antibody to a column material, which then selectively binds the biological product, while everything else flows through.

Inclusion bodies upon solubilization exposes hydrophobic groups while there remain chemical groups on denatured proteins capable of binding to resin (Singh and Panda, 2005), allowed separation of these proteins during the stages of refolding to native state.

Some of the state of the art resins binding technologies include:

a. Novozymes's newly patented Dual Affinity Polypeptide technology platform replaces Protein A process steps with similar, but disposable, technology.
b. Stimuli responsive polymers enable complexation and manipulation of biological products and allow for control of polymer and biological product complex solubility, which results in the direct capture of the product without centrifuges or Protein A media, from Millipore Corp.
c. Mixed mode sorbents to replace traditional Protein A and ion exchange, for improved selectivity and capacity with shorter residence times. These media, with novel chemistries, include hydrophobic charge induction chromatography, such as MEP, and Q and S HyperCel from Pall Corp.
d. Monoliths, involving chromatography medium as a single-piece homogeneous column, such as Convective Interaction Media monolithic columns from BIA Separations.
e. Simulated moving beds, involving multicolumn countercurrent chromatography, such as BioSMB from Tarpon Biosystems.
f. Protein G (multiple vendors).
g. Single domain camel-derived (camelid) antibodies to IgG, such as CaptureSelect from BAC.
h. New inorganic ligands, including synthetic dyes, such as Mabsorbent A1P and A2P from Prometic Biosciences.
i. Expanded bed adsorption chromatography systems, such as the Rhobust platform from Upfront Chromatography.
j. Ultra-durable zirconia oxide-bound affinity ligand chromatography media from ZirChrom Separations.
k. Fc-receptor mimetic ligand from Tecnoge.
l. ADSEPT (ADvanced SEParation Technology) from Nysa Membrane Technologies.
m. Membrane affinity purification system from PurePharm Technologies.
n. Custom-designed peptidic ligands for affinity chromatography from Prometic Biosciences, Dyax, and others.
o. Protein A- and G-coated magnetic beads, such as from Invitrogen/Dynal.
p. New affinity purification methods based on expression of biological products or MAbs as fusion biological products with removable portion (tag) having affinity for chromatography media, such as histidine) tags licensed by Roche (Genentech).

q. Protein A alternatives in development, including reverse micelles (liposomes), liquid-nutrient medium extraction systems, crystallization, immobilized metal affinity chromatography, and novel membrane chromatography systems.

r. Plug-and-play solutions with disposable components (e.g., ReadyToProcess), process development AKTA with design of experiments capability, and multicolumn continuous capture, from GE Healthcare.

It is surprising that while great advances have been made in the design of resins available to capture biological products, these have been only used in the downstream processing of purification. Adding resins to a crude mixture of biological products and host cells will be no different than the current process that simply concentrates the same medium and loads it onto columns with all of the impurities in it. The only difference will be that when practiced at the end of the bioreaction cycle, this will require sufficient resin to bind almost the entire biological product. Aiming at a cell line that produces 1 mg/mL of protein and that the binding capacity of the resin used is 50 mg/mL, this will require 20 L of resin when operating a 1000 L bioreactor. The cost of resins suitable for the manufacturing of monoclonal antibodies can range from $15-$20,000 per liter, such as Protein A. As a result, most manufacturers would rather run several sub-batches of purification using a smaller quantity of the resin. However, given that these can be used for hundreds of times, the cost is readily amortized for use and avoids the tediousness and regulatory hurdles in preparing sub-batches.

While a larger quantity of resin is added at the end of process treatment, these additions are spread over time if the present invention is used where the classical perfusion method is replaced with resin capture. By adding various amounts of resin as the bioreaction proceeds, the expressed protein is removed from the nutrient medium. It is important not to add a larger quantity of resin than needed at any given time since it is inevitable that other components in the nutrient medium get lost to resin as well if the resin used has a non-specific binding characteristics. This would not be the case if an immune-affinity or specific structure resins such as Protein A is used. Where it is inevitable to lose nutrients to the resin, these should be replaced along with the addition of resin to the biroeactor. Some caution is necessary when using a resin to bind proteins during the process of bioreaction as these must be properly sterilized. It is for this reason, it may be advantageous to use a more specific binding resin that can be added during the sterilization of the container by gamma radiation.

Additionally, one embodiment of the invention may be practiced by using the least expensive resins to generically bind all soluble organic components and then elute them instantly using a buffer without any concern for the profile of elution to separate these components. Such generic resins are very inexpensive and may not even have to be reused.

The present invention thus offers a method of biological product harvesting and purification in the same bioreactor where the biological product is produced.

Applications

In the present invention, compositions comprising nonbiologic components include, but are not limited to, those which comprise microcarriers (e.g., polymer spheres, solid spheres, gelatinous particles, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, cells, capillaries, and aggregates (e.g., aggregates of cells).

The biological components that may be processed in accordance with the invention are described in the paragraphs which follow and include, but are not limited to, cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts), bacteria, fungi, and yeast.

Illustrative animal cells include Chinese hamster ovary (CHO), mouse myeloma, M0035 (NS0 cell line), hybridomas (e.g., B-lymphocyte cells fused with myeloma tumor cells), baby hamster kidney (BHK), monkey COS, African green monkey kidney epithelial (VERO), mouse embryo fibroblasts (NIH-3T3), mouse connective tissue fibroblasts (L929), bovine aorta endothelial (BAE-1), mouse myeloma lymphoblastoid-like (NS0), mouse B-cell lymphoma lymphoblastoid (WEHI 231), mouse lymphoma lymphoblastoid (YAC 1), mouse fibroblast (LS), hepatic mouse (e.g., MC/9, NCTC clone 1469), and hepatic rat cells (e.g., ARL-6, BRL3A, H4S, Phi 1 (from Fu5 cells)).

Illustrative human cells include retinal cells (PER-C6), embryonic kidney cells (HEK-293), lung fibroblasts (MRC-5), cervix epithelial cells (HELA), diploid fibroblasts (WI38), kidney epithelial cells (HEK 293), liver epithelial cells (HEPG2), lymphoma lymphoblastoid cells (Namalwa), leukemia lymphoblastoid-like cells (HL60), myeloma lymphoblastoid cells (U 266B1), neuroblastoma neuroblasts (SH-SY5Y), diploid cell strain cells (e.g., propagation of poliomyelitis virus), pancreatic islet cells, embryonic stem cells (hES), human mesenchymal stem cells (MSCs, which can be differentiated to osteogenic, chondrogenic, tenogenic, myogenic, adipogenic, and marrow stromal lineages, for example), human neural stem cells (NSC), human histiocytic lymphoma lymphoblastoid cells (U937), and human hepatic cells such as WRL68 (from embryo cells), PLC/PRF/5 (i.e., containing hepatitis B sequences), Hep3B (i.e., producing plasma proteins: fibrinogen, alpha-fetoprotein, transferrin, albumin, complement C3 and/or alpha-2-macroglobulin), and HepG2 (i.e., producing plasma proteins: prothrombin, antithrombin III, alpha-fetoprotein, complement C3, and/or fibrinogen).

Cells from insects (e.g., baculovirus and *Spodoptera frugiperda* ovary (Sf21 cells produce Sf9 line)) and cells from plants or food, may also be cultured in accordance with the invention. Cells from sources such as rice (e.g., *Oryza sativa*, *Oryza sativa* cv Bengal callus culture, and *Oryza sativa* cv Taipei 309), soybean (e.g., *Glycine max* cv Williams 82), tomato (*Lycopersicum esculentum* cv Seokwang), and tobacco leaves (e.g., *Agrobacterium tumefaciens* including Bright Yellow 2 (BY-2), *Nicotiana tabacum* cv NT-1, *N. tabacum* cv BY-2, and *N. tabacum* cv Petite Havana SR-1) are illustrative examples.

Bacteria, fungi, or yeast may also be cultured in accordance with the invention. Illustrative bacteria include *Salmonella*, *Escherichia coli*, *Vibrio cholerae*, *Bacillus subtilis*, *Streptomyces*, *Pseudomonas fluorescens*, *Pseudomonas putida*, *Pseudomonas* sp, *Rhodococcus* sp, *Streptomyces* sp, and *Alcaligenes* sp. Fungal cells can be cultured from species such as *Aspergillus niger* and *Trichoderma reesei*, and yeast cells can include cells from *Hansenula polymor-* pha, *Pichia pastoris, Saccharomyces cerevisiae, S. cerevisiae* crossed with *S. bayanus, S. cerevisiae* crossed with LAC4 and LAC1-2 genes from *K. lactis, S. cerevisiae* crossed with *Aspergillus shirousamii, Bacillus subtilis, Saccharomyces diastasicus, Schwanniomyces occidentalis, S. cerevisiae* with genes from *Pichia stipitis*, and *Schizosaccharomyces pombe*.

Products

A variety of different products may also be produced in accordance with the invention. Illustrative products include proteins (e.g., antibodies and enzymes), vaccines, viral products, hormones, immunoregulators, metabolites, fatty acids, vitamins, drugs, antibiotics, cells, and tissues. Non-limiting examples of proteins include human tissue plasminogen activators (tPA), blood coagulation factors, growth factors (e.g., cytokines, including interferons and chemokines), adhesion molecules, Bcl-2 family of proteins, polyhedrin proteins, human serum albumin, scFv antibody fragment, human erythropoietin, mouse monoclonal heavy chain 7, mouse $IgGn_{2b/k}$, mouse IgG1, heavy chain mAb, Bryondin 1, human interleukin-2, human interleukin-4, ricin, human α1-antitrypisin, biscFv antibody fragment, immunoglobulins, human granulocyte, stimulating factor (hGM-CSF), hepatitis B surface antigen (HBsAg), human lysozyme, IL-12, and mAb against HBsAg. Examples of plasma proteins include fibrinogen, alpha-fetoprotein, transferrin, albumin, complement C3 and alpha-2-macroglobulin, prothrombin, antithrombin III, alpha-fetoprotein, complement C3 and fibrinogen, insulin, hepatitis B surface antigen, urate oxidase, glucagon, granulocyte-macrophage colony stimulating factor, hirudin/desirudin, angiostatin, elastase inhibitor, endostatin, epidermal growth factor analog, insulin-like growth factor-1, kallikrein inhibitor, α1-antitrypsin, tumor necrosis factor, collagen protein domains (but not whole collagen glycoproteins), proteins without metabolic byproducts, human albumin, bovine albumin, thrombomodulin, transferrin, factor VIII for hemophilia A (i.e., from CHO or BHK cells), factor VIIa (i.e., from BHK), factor IX for hemophilia B (i.e., from CHO), human-secreted alkaline phosphatase, aprotinin, histamine, leukotrienes, IgE receptors, N-acetylglucosaminyltransferase-III, and antihemophilic factor VIII.

Enzymes may be produced from a variety of sources using the invention. Non-limiting examples of such enzymes include YepACT-AMY-ACT-X24 hybrid enzyme from yeast, *Aspergillus oryzae* α-amylase, xylanases, urokinase, tissue plasminogen activator (rt-PA), bovine chymosin, glucocerebrosidase (therapeutic enzyme for Gaucher's disease, from CHO), lactase, trypsin, aprotinin, human lactoferrin, lysozyme, and oleosines.

Vaccines also may be produced using the invention. Non-limiting examples include vaccines for prostate cancer, human papilloma virus, viral influenza, trivalent hemagglutinin influenza, AIDS, HIV, malaria, anthrax, bacterial meningitis, chicken pox, cholera, diphtheria, haemophilus influenza type B, hepatitis A, hepatitis B, pertussis, plague, pneumococcal pneumonia, polio, rabies, human-rabies, tetanus, typhoid fever, yellow fever, veterinary-FMD, New Castle's Disease, foot and mouth disease, DNA, Venezuelan equine encephalitis virus, cancer (colon cancer) vaccines (i.e., prophylactic or therapeutic), MMR (measles, mumps, rubella), yellow fever, *Haemophilus influenzae* (Hib), DTP (diphtheria and tetanus vaccines, with pertussis subunit), vaccines linked to polysaccharides (e.g., Hib, Neisseria meningococcus), *Staphylococcus pneumoniae*, nicotine, multiple sclerosis, bovine spongiform encephalopathy (mad cow disease), IgG1 (phosphonate ester), IgM (neuropeptide hapten), SIgA/G (*Streptococcus mutans* adhesin), scFv-bryodin 1 immunotoxin (CD-40), IgG (HSV), LSC(HSV), Norwalk virus, human cytomegalovirus, rotavirus, respiratory syncytial virus F, insulin-dependent autoimmune mellitus diabetes, diarrhea, rhinovirus, herpes simplex virus, and personalized cancer vaccines, e.g., for lymphoma treatment (i.e., in injectable, oral, or edible forms). Recombinant subunit vaccines also may be produced, such as hepatitis B virus envelope protein, rabies virus glycoprotein, *E. coli* heat labile enterotoxin, Norwalk virus capsid protein, diabetes autoantigen, cholera toxin B subunit, cholera toxin B an dA2 subunits, rotavirus enterotoxin and enterotoxigenic *E. coli*, fimbrial antigen fusion, and porcine transmissible gastroenteritis virus glycoprotein S.

Viral products also may be produced. Non-limiting examples of viral products include sindbis, VSV, oncoma, hepatitis A, channel cat fish virus, RSV, corona virus, FMDV, rabies, polio, reo virus, measles, and mumps.

Hormones also may be produced using the invention. Non-limiting examples of hormones include growth hormone (e.g., human growth hormone (hGH) and bovine growth hormone), growth factors, beta and gamma interferon, vascular endothelial growth factor (VEGF), somatostatin, platelet-derived growth factor (PDGF), follicle stimulating hormone (FSH), luteinizing hormone, human chorionic hormone, and erythropoietin.

Immunoregulators also may be produced. Non-limiting examples of immunoregulators include interferons (e.g., beta-interferon (for multiple sclerosis), alpha-interferon, and gamma-interferon) and interleukins (such as IL-2).

Metabolites (e.g., shikonin and paclitaxel) and fatty acids (i.e., including straight-chain (e.g., adipic acid, Azelaic acid, 2-hydroxy acids), branched-chain (e.g., 10-methyl octadecanoic acid and retinoic acid), ring-including fatty acids (e.g., coronaric acid and lipoic acid), and complex fatty acids (e.g., fatty acyl-CoA)) also may be produced.

Organ growth, cell and gene therapy.

Bioreactor Assembly

The containers useful in the various embodiments of the invention may be of any size suitable for containing a nutrient medium. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible. Preferably, the container volume will range between about 1 L and 1000 L, and more preferably between about 5 L and 500 L, and even more preferably between 5 L and 200 L.

The components of the bioreactors and other devices described herein which come into contact with the nutrient medium or products provided thereby desirably comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

Desirably the containers comprise biocompatible materials, more desirably biocompatible polymers. When collapsible containers are selected for use, the container may be supported by or may line an inner surface of a support structure, e.g., the outer support housing having container-retaining sidewalls. However, the invention may be practiced using non-collapsible or rigid containers or conduits.

The containers may have any thickness suitable for retaining the nutrient medium therewithin, and may be designed to have a certain resistance to puncturing during operation or while being handled. For example, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In certain embodiments, the container may include more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container.

It thus should be understood that a container may be formed of any suitable combinations of layers. The container (e.g., collapsible bag) may include, for example, 1 layer, greater than or equal to 2 layers, greater than or equal to 3 layers, or greater than or equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In addition, the container preferably is seamless in order to improve its strength and avoid deposition of growing cells in the media.

In addition, the container preferably is cylindrical in order to keep the distance between the sparging filter and the outer wall of the container.

All or portions of the container also are desirably translucent, or more desirably transparent, to allow viewing of contents inside the container. The latter is preferred when it is desirable to irradiate the nutrient medium within the container.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described in terms of specific embodiments and applications, persons skilled in the art, can in light of this teaching, generate additional embodiments without exceeding the scope or departing from the spirit of the claimed invention. The specific composition of the various elements of the perfusion bioreactor system, for example, should not be construed as a limiting factor. Accordingly, it is to be understood that the drawings and descriptions in this disclosure are proffered to facilitate comprehension of the invention and should not be construed to limit the scope thereof.

REFERENCES

Fenge et al., "Agitation, aeration and perfusion modules for cell culture bioreactors," Cytotechnology 11, pgs. 233-244 (1993).

Henzler et al., "Oxygenation of cell cultures," Bioprocess Eng. 9, pgs. 61-75 (1993)

Krahe M., "Biochchemical Engineering," Reprint from Ullmann's Encyclopedia of Indus. Chem.; VCH Publishers: Weinheim, Germany, Vol. 6.

Vorlop J. et al., Entwicklung eines Membranruhrers zur blasenfreien Begasung and Durchmischung von Zellkulturreaktoren im PilotmaBstab, PhD Thesis, Technical Univ. Braunschweig, Germany (1989).

Nelson, K. L. et al., "Industrial scale mammalian cell culture, Part I: Bioreactor design consdiderations," BioPharm., 1, pgs. 42-46 (1988).

Nehring et al., "Experimental study of a ceramic microsparging aerations system in a pilot scale animal cell culture," Biotechnol. Progress, 20, pgs 1710-1717 (2004).

Marks, D. M., "Equipment design consideration for large scale cell culture," Cytotechnology, 42, pgs. 21-33 (2003).

Chisti, Y. "Animal-cell damage in sparged bioreactors," Trends Biotechnol," 18, pgs. 420-432 (2000).

Papoutsakis E. T. et al., "Fluid-mechanical damage of animal cells in bioreactors," Tibtech, 9, pgs. 427-437 (1991).

Chalmers J. J. et al., "Cells and bubbles in sparged bioreactors," Cytotechnology, 15, pgs 311-320 (1994).

Kunas K. T. et al., "Damage mechanisms of suspended animal cells in agitated bioreactors with and without bubble entrainment," Biotechnology and Bioengineering, 36, pgs 476-483 (1990).

Nehring D., Czermak, P., "Ein neues Begasungssystem fur Zelkulturen im Labor-und ProduktionsmaBstab, in Bechmann, D. (Hrsg.); Technische System fur Biotechnologie und U"mwelt—Biosensorik und Zelkulturtechnik, S. 265-272, ISBN 3-503-06645-4, Erich Schmidt Verlag, Berlin (2002).

Zhang S. et al., "A comparison of oxygen methods for high-density perfusion cultures of animal cells," Biotechnology and Bioengineering, 41, pgs. 685-692 (1993).

Martens, D.; Tramper, J. "Lethal events during gas sparging animal cell culture," Biotechnology and Bioengineering, 37, pgs 484-490 (1991).

Michaels, J. D. et al., "Sparging and agitation-induced injury of cultured animal cells: do cell-to-bubble interactions in the bulk liquid injure cells?" Biotechnology and Bioengineering, 51, pgs. 399-409 (1996).

Meier S. J.; Hatton, T. A.; Wang, D. I. C. "Cell death from bursting bubbles; role of cell attachment to rising bubbles in sparged reactors," Biotechnology and Bioengineering, 62, pgs 468-478 6 (1999).

I claim:

1. A closed bioreactor, suitable for use in uncontrolled environment, comprising:
   a) a container comprising a nutrient medium and a biological culture;
   b) at least one gas outlet tube comprising an in line cartridge connected to the gas outlet comprising a carbon dioxide absorbent material;
   c) at least one gas inlet connected to the container comprising a tube for introducing gas into the container and wherein the gas inlet is also connected to the gas outlet through a tube allowing the gas to recirculate within the container, and wherein the gas inlet is connected to a source of gas;
   d) at least one liquid port for adding liquid to the container, wherein the liquid port is connected to the container and comprises a tube extending below the surface of the nutrient medium;
   e) a sterilizing filter capable of removing contaminants installed between the source of gas and the gas inlet;
   f) a stopcock installed between the sterilizing filter (e) and the gas inlet;
   g) a sterilizing filter capable of removing contaminants installed at the liquid port;
   h) a stopcock installed between sterilizing filter (g) and the liquid port;
   i) a peristaltic pump installed in the tube connected between the gas outlet and the gas inlet; and
   j) at least one sparger connected to the gas inlet and located in the container.

2. The closed bioreactor according to claim 1, further comprising an outer support housing providing support to said container.

3. The closed bioreactor according to claim 1, further comprising a filter drain capable of retaining particles larger than 5μ.

4. The closed bioreactor according to claim 1, wherein the biological culture is a human cell, an animal cell, a bacterium, a plant cell, yeast, or fungi.

5. The closed bioreactor according to claim 1, further comprising a plurality of remotely operated sensors.

6. The closed bioreactor according to claim 5, wherein the remotely operated sensors comprise oxygen and carbon dioxide sensors.

7. The closed bioreactor according to claim 1, further comprising a temperature controller for the nutrient medium.

8. The closed bioreactor according to claim 1, wherein the container is comprised of a material that is disposable.

9. The closed bioreactor according to claim 1, wherein the container is comprised of a flexible polymer.

10. The closed bioreactor according to claim 1, wherein the container comprises a biocompatible polymer.

11. The closed bioreactor according to claim 1, wherein the carbon dioxide absorbent material is selected from the group of absorbent materials comprising soda lime, calcium hydroxide, sodium hydroxide, potassium hydroxide, lithium hydroxide, lithium silicate, lithium zirconate, lithium oxide, activated charcoal, zeolite and an ion exchange resin.

* * * * *